US 9,464,966 B2

(12) United States Patent
Munier et al.

(10) Patent No.: US 9,464,966 B2
(45) Date of Patent: Oct. 11, 2016

(54) DEVICE FOR SAMPLING SOLIDS FROM A SEALED ENCLOSURE AND METHOD USING SAME

(71) Applicant: AXENS, Rueil Malmaison (FR)

(72) Inventors: Michel Munier, Le Châtelet en Brie (FR); Jean Paul Gouzard, Rueil Malmaison (FR); Rémi Girod, Paris (FR)

(73) Assignee: AXENS, Rueil Malmaison (FR)

(*) Notice: Subject to any disclaimer, the term of this patent is extended or adjusted under 35 U.S.C. 154(b) by 304 days.

(21) Appl. No.: 14/298,994

(22) Filed: Jun. 9, 2014

(65) Prior Publication Data
US 2014/0366654 A1 Dec. 18, 2014

(30) Foreign Application Priority Data
Jun. 12, 2013 (FR) ...................... 13 55441

(51) Int. Cl.
G01N 1/20 (2006.01)
G01N 1/04 (2006.01)
G01N 1/08 (2006.01)
B01J 8/02 (2006.01)

(52) U.S. Cl.
CPC . *G01N 1/04* (2013.01); *B01J 8/02* (2013.01); *G01N 1/08* (2013.01); *G01N 1/20* (2013.01); *B01J 2208/00884* (2013.01); *B01J 2208/00982* (2013.01)

(58) Field of Classification Search
CPC ............ B01J 2208/00884; B01J 2208/00982; B01J 8/02; G01N 1/04; G01N 1/08
USPC ............. 73/863.42, 863.43, 863.45, 863.51, 73/863.52, 863.54, 863.56, 863.01, 73/863.81, 53.01, 53.07, 61.59, 863.85
See application file for complete search history.

(56) References Cited

U.S. PATENT DOCUMENTS

| | | | | |
|---|---|---|---|---|
| 2,738,679 A | * | 3/1956 | Senkowski | G01N 1/20 73/863.43 |
| 3,066,539 A | * | 12/1962 | Coker | G01N 1/04 73/863.54 |
| 3,348,419 A | * | 10/1967 | Addison | B01J 8/002 73/863.83 |
| 3,653,265 A | * | 4/1972 | Vallino | B01J 8/0005 73/863.83 |
| 3,751,991 A | * | 8/1973 | Fisher | G01N 1/20 73/863.02 |
| 3,786,682 A | * | 1/1974 | Winter | G01N 1/20 73/863.86 |
| 3,868,854 A | * | 3/1975 | Travor | G01N 1/08 137/318 |
| 4,009,618 A | * | 3/1977 | Chatham | G01N 1/20 73/863.83 |
| 4,215,579 A | * | 8/1980 | Hines | G01N 1/20 73/863.53 |
| 4,771,641 A | * | 9/1988 | Beltrop | G01N 1/20 763/863.31 |

(Continued)

FOREIGN PATENT DOCUMENTS

FR 2317642 A1 2/1977

*Primary Examiner* — Eric S McCall
*Assistant Examiner* — Mohammed E Keramet-Amircola
(74) *Attorney, Agent, or Firm* — Fitch, Even, Tabin & Flannery LLP

(57) ABSTRACT

The present invention is a device (14) for sampling a solid from a sealed enclosure (12). The device comprises a body (18) carrying a sampling head (16) with a solid collection recess (28), a collected solid transfer recess (28') and an angular-displacement shutter means (30) for the recesses controlled by the control means (48). The device also comprises means (78, 80) for limiting the angular clearance of the shutter means for no-load displacement (c) of the means.

17 Claims, 3 Drawing Sheets

(56) References Cited

U.S. PATENT DOCUMENTS

| | | | | |
|---|---|---|---|---|
| 4,771,642 A * | 9/1988 | Parth | ............ | G01N 1/20 73/863.21 |
| 6,945,129 B2 * | 9/2005 | Escal | ............ | B04B 5/0421 422/64 |
| 7,168,332 B2 * | 1/2007 | Orange | ............ | G01N 1/20 73/863.41 |
| 7,363,830 B2 * | 4/2008 | Girard | ............ | G01N 1/14 73/863.42 |
| 7,765,882 B2 * | 8/2010 | Greten | ............ | G01N 1/20 366/131 |
| 2003/0033890 A1 * | 2/2003 | Rodgers | ............ | G01N 1/2211 73/863.43 |
| 2010/0101337 A1 * | 4/2010 | Mann | ............ | G01N 1/04 73/863.43 |

* cited by examiner

DEVICE FOR SAMPLING SOLIDS FROM A SEALED ENCLOSURE AND METHOD USING SAME

CROSS REFERENCE TO RELATED APPLICATION

Reference is made to French Application Serial No. 13/55.441, filed Jun. 12, 2013, which application is incorporated herein by reference in its entirety.

BACKGROUND OF THE INVENTION

1. Field of the Invention

The present invention relates to a device for sampling solids from a sealed enclosure such as, for example, a silo, a hopper, a reactor, a regenerator or an adsorber, and to a method using the same. The invention more particularly relates to a sampling device allowing gravity sampling of the solid samples in form of granules, extrudates, balls, like those used for a catalyst or an adsorbent for example.

2. Description of the Prior Art

When divided solids are fed into enclosures operating under high pressure and/or temperature conditions or when they are arranged in enclosures where they are stored or transported by gravity, it is often necessary to take a sample of the solid.

The main purpose of this sampling is to check the mechanical or physico-chemical properties of the solid and thus to detect possible impurities settled at the surface thereof or to monitor the evolution of the quality of the stored solid stored or the solid in motion.

Sampling notably allows understanding the reasons for a possible malfunction, to check the solid storage behavior over time or to predict the maximum operation time for the solid and thus to fix or to anticipate possible problems.

In the case of refinery plants using divided solids, it may also facilitate monitoring of the unit comprising the content of the enclosure, a catalytic reactor for example, and thus enable the operation thereof to be optimized.

U.S. Pat. No. 4,009,618 notably discloses a sampling device allowing taking of samples of solid materials from a sealed enclosure such as a reactor, for example, providing catalytic cracking of hydrocarbons in the presence of a catalyst. These samplings are performed using a sampling head fed into the enclosure and carried by the body of the device. This head comprises a receptacle provided with a recess in the upper and lower part, and two slotted rotary discs driven in rotation by a shaft controlled by any known means. During a first rotation of these discs, a solid sample enters the receptacle through the upper recess controlled by one of the discs while the other disc seals the recess in the lower part. After another rotation of these discs, the upper recess is sealed by one of the discs while the other disc clears the recess in the lower part so that the solid sample is sent to a collection means.

However, the drawback of such devices is that they may jam during solid sampling operations.

Indeed, jamming can be due to the solid that may be partly crushed and/or stuck in certain moving parts, to scratches present on the constituent parts of the sampling device, or to expansions occurring on mobile parts with narrow tolerance ranges.

Depending on the more or less frequent use and on the operating conditions, the device can have operability problems as a result of the jamming of the various mobile parts, or it can even be out of order when the mobile parts are stuck.

In order to overcome this drawback, pneumatic devices or devices using gas flows for conveying the solid are provided, as described, for example, in U.S. Pat. Nos. 3,653,265 or 3,786,682. These devices allow mechanical problems to be avoided, but they involve the drawback of conveying small amounts of solid during sampling.

SUMMARY OF THE INVENTION

The present invention overcomes the aforementioned drawbacks with a simple solid sampling device which prevents jamming of the mobile parts of the sampling head without increasing the frequency of use of the device and without influencing the amount of solid sampled. This jamming can be generated by certain types of solids or when the sampling operations are conducted at a low frequency.

The invention therefore is a device for sampling a solid from a sealed enclosure, the device comprising a body carrying a sampling head with a solid collection recess, a collected solid transfer recess, angular-displacement shutter means for the recesses controlled by a control means, characterized in that the device also comprises means for limiting the angular clearance of the shutter means for no-load displacement of the means.

The control means can comprise a rod connected to the shutter means and the limiting means can comprise stops with at least one of the stops being removable, for limiting the angular displacement.

The rod can be connected to an operating lever cooperating with the stops.

The rod can carry a torsion spring means for circumferential bearing of the lever on one of the stops.

The control means can comprise a rod connected to the shutter means and to a geared motor with two directions of rotation fitted with an end position detection device for limiting the no-load angular displacement (c) of the shutter means.

The control means can comprise a rod connected to the shutter means and to a cam controlled by a cylinder.

The control means can comprise a rod connected to the shutter means and carrying a pinion cooperating with a rack carried by a cylinder, and limitation of the no-load angular displacement (c) of the shutter means can be provided by the stroke of the cylinder piston.

The shutter means can comprise a cup provided with an axial hollow running through the cup.

The invention also relates to a device that can be used for taking catalyst samples in an enclosure isolated from the atmosphere.

The invention also relates to a device that can be used for taking catalyst samples in an oil refining unit.

The invention also relates to a device that can be used for taking catalyst samples in a reforming unit.

The invention furthermore relates to a method of using a device for sampling a solid from a sealed enclosure, the device comprising a sampling head with a solid collection recess, a collected solid transfer recess and angular-displacement shutter means for the recesses controlled by a control means, characterized in that it achieves a no-load angular displacement (c) of the shutter means to prevent jamming of the shutter means and/or of the control means.

The method can achieve the no-load angular displacement according to the shutter means without allowing collection of the solid through the sampling head.

The method can achieve the no-load angular displacement periodically.

The method can achieve the no-load angular displacement with a weekly periodicity.

BRIEF DESCRIPTION OF THE DRAWINGS

Other features and advantages of the invention will be clear from reading the description hereafter, given by way of non limitative example, with reference to the accompanying figures wherein.

DETAILED DESCRIPTION OF THE INVENTION

Figure 1:
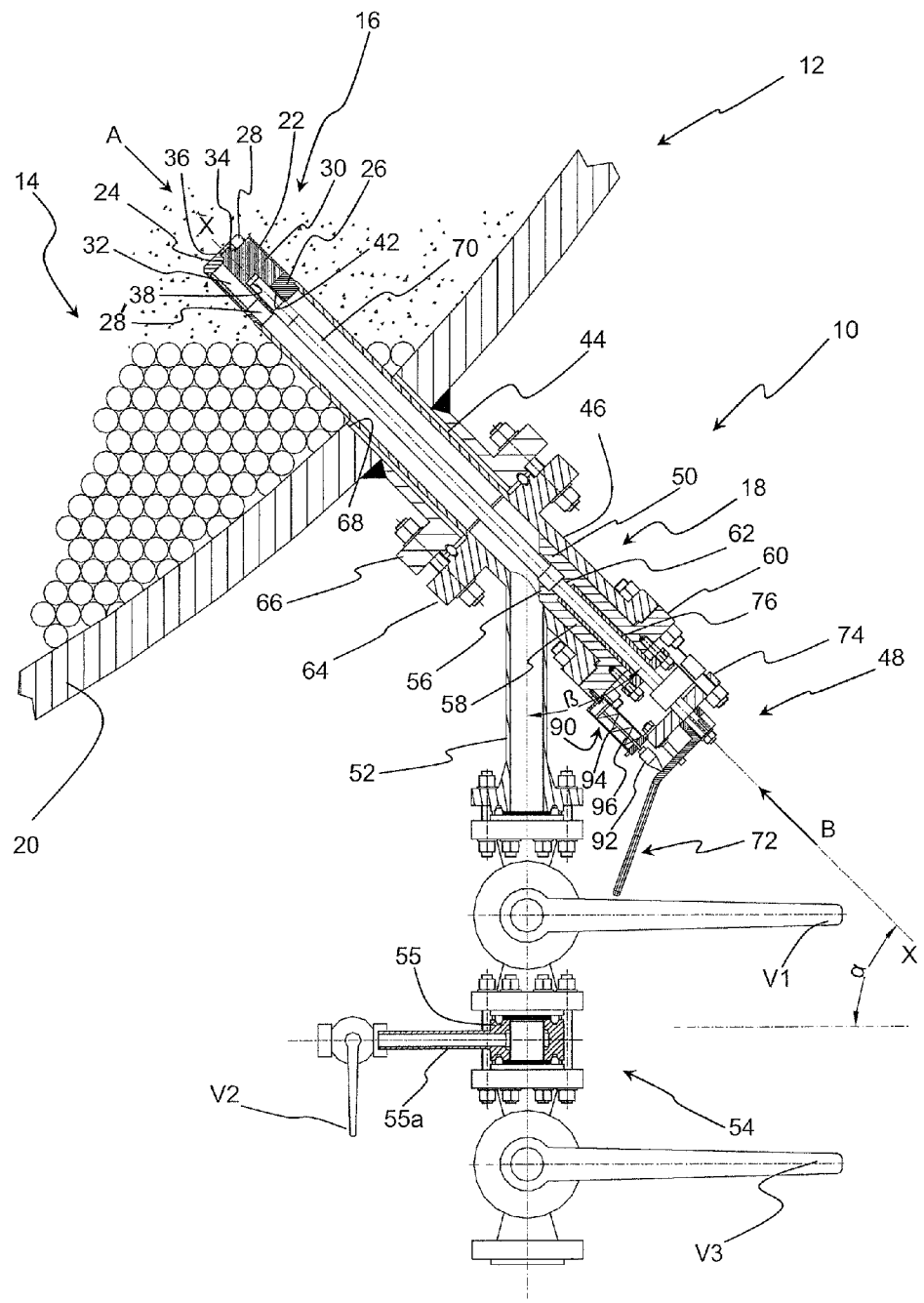
FIG. 1 is a partial cross-sectional view of the sampling device according to the invention.

In the example shown in FIG. 1, a sampling device 10 is arranged on an enclosure 12, preferably sealed and advantageously isolated from the atmosphere, containing divided solids 14.

Advantageously, this sampling device can be used when the enclosure is in operation or at standstill.

The enclosure that is described in the rest of the description, by way of example only, is a fixed-bed catalysis reactor, but any other enclosure such as a silo, a hopper, a regenerator or an adsorber also may be used in the practice of the invention.

The solids contained in this enclosure are solid particles in form of granules, extrudates or balls.

The sampling device comprises a head 16 for taking solid samples within this enclosure, carried by a tubular body 18 of longitudinal axis XX running through wall 20 of reactor 12.

Figure 2:
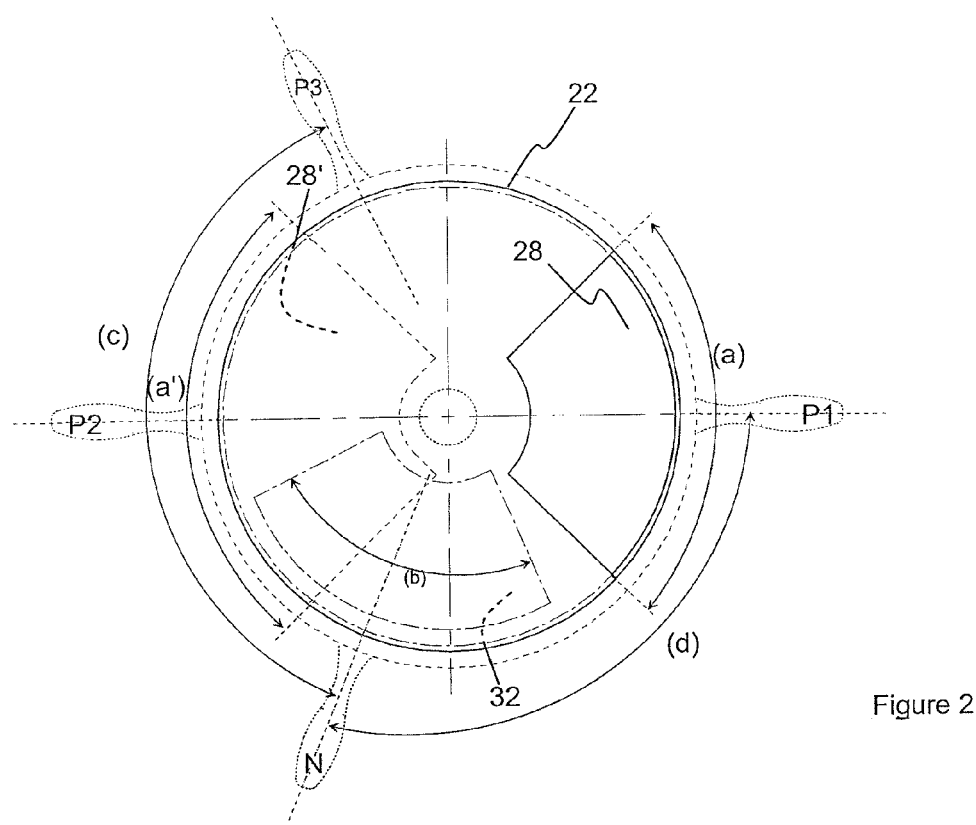
FIG. 2 is an end view in the direction of arrow A of the sampling device of FIG. 1.
Figure 3:
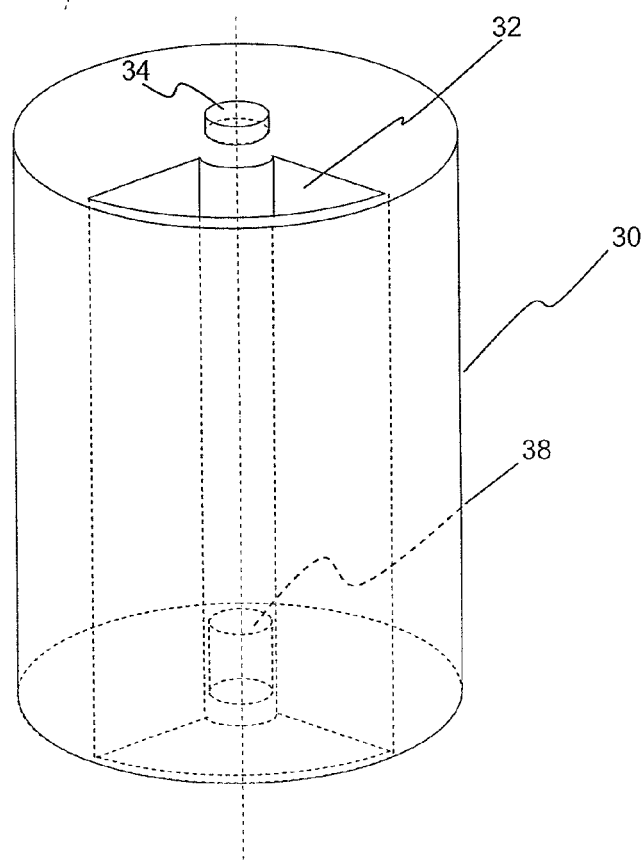
FIG. 3 is a perspective view of one of the elements of the sampling device.

In addition, with reference to FIGS. 2 and 3, the head works on the principle of a deflector allowing taking a predetermined amount of solid particles and avoiding a flow in larger amount.

This head comprises a cylindrical housing 22, circular here, having a longitudinal axis coinciding with that of the body while being closed in the upper part thereof by a cover 24 and, in the lower part thereof, by a bottom 26. The cover and the bottom are each provided with a recess 28 and 28' in the form of angular sectors (a) and (a').

The inside of the housing contains a recess sealing cup 30 in form of a full cylindrical section part of longitudinal axis coincident with the axis of the housing. The diameter of this cup substantially corresponds to that of the inside of the housing and the height thereof is substantially equal to that of this housing, which allows the cup to freely rotate inside the housing, and between the cover and the bottom.

This cup is provided with a hollow 32 substantially parallel to the longitudinal axis and running right through the cup. Advantageously, hollow 32 has a cross section in form of angular sector (b) whose shape corresponds to the angular sector of the cover and of the bottom.

Preferably, angular sector (a) of the cover has dimensions and a sector angle smaller than the cup hollow, whereas angular sector (a') of the bottom has dimensions and a sector angle larger than those of the angular section of the cup hollow. The volume of the hollow thus allows determination of the solid sampling volume.

This cup is fitted, on the upper plane face thereof, with a locating pin 34 coaxial to the axis of the cup, which cooperates with a blind bore 36 provided on the inner face of the cover. On the lower plane face thereof, the cup comprises a bore 38 intended to receive a rotating control that is described in detail hereafter. To allow this control to be connected to the cup, bottom 28 is provided with a perforation 42 corresponding with bore 38.

In connection with FIG. 1, body 18, that is advantageously arranged below enclosure 12, is inclined at an angle α ranging between 30° and 90° to the horizontal.

This body comprises an upper tubular extension 44, of circular shape here, which partly penetrates the enclosure and supports the sampling head for the solid contained in this enclosure. This body also comprises a lower tubular extension 46 containing various means 48 for controlling the rotation of cup 30.

The lower tubular extension also comprises a deflection member 50 housed and fastened within this extension for driving the sample towards a tubular pipe 52 leading to an air lock 54.

The air lock is comprised of three valves V1, V2, V3 and of a tubular part 55 carrying a line 55a substantially orthogonal to tubular part 55 and connected to valve V2.

Depending on the valve opening and closing sequence, it is possible to isolate the sample located in tubular part 55, then to discharge it through line 55a and eventually to collect it in any reception means.

The deflection member has a deflection surface 56 carried by a tubular sleeve 58 with an angle to the vertical allowing gravity flow of the solid sample towards the air lock. This angle preferably ranges between 0° and 60°, more preferably between 5° and 45°, and most preferably between 10° and 30°. This member also comprises a fastening baseplate 60 on the lower end of the body, as well as a longitudinal axial bore 62 starting from the deflection surface and leading to baseplate 60.

Pipe 52 is oriented at an angle 13 generally ranging between 10° and 90°, preferably between 20° and 70°, and more preferably between 30° and 60°, or even between 40° and 50° with respect to axis XX of the body.

As can be better seen in FIG. 1, the body is provided with a clamp 64 for assembly on a sole 66 fastened to the outside of wall 20 and surrounding a pass-through hole 68 for the upper tubular extension.

By combining FIG. 1 and FIGS. 4, 5 and 6, rotation control means 48 for cup 30 comprise a driving rod 70 running right through body 18 and deflection member 50 by extending from this cup to the outside of the lower end of the body where it is connected to an operating lever 72 arranged outside the body.

The upper end of this rod is connected to cup 30 through bore 38 by any known means, such as screwing or male-female jointing, while the lower end of this rod is fixedly connected to the lever, preferably by keying and screwing.

Advantageously, a circular plate 74 is housed between the operating lever and the lower end of the body by being fastened to the baseplate of the deflection member. Fastening can for example be provided by a system combining pins and nuts. This fastening thus allows prevention of the plate from being rotated when lever 72 is actuated and it serves as an axial stop for the rod through the agency of the lever.

Furthermore, a sealing device 76, more commonly referred to as stuffing box, is housed between rod 70 and bore 62. This device thus allows absorbing the temperature and pressure differences between the enclosure and outside.

The plate carries angular clearance limiting means for the lever and therefore for the cup to which it is connected through the rod. These limiting means include angle stops 78 and 80 arranged with an angular distance allowing limiting the rotational clearance of the lever within an angular range (c) between these two stops.

Stops 78 and 80 are totally or partly removable to allow complete rotation of the lever.

Figure 4:
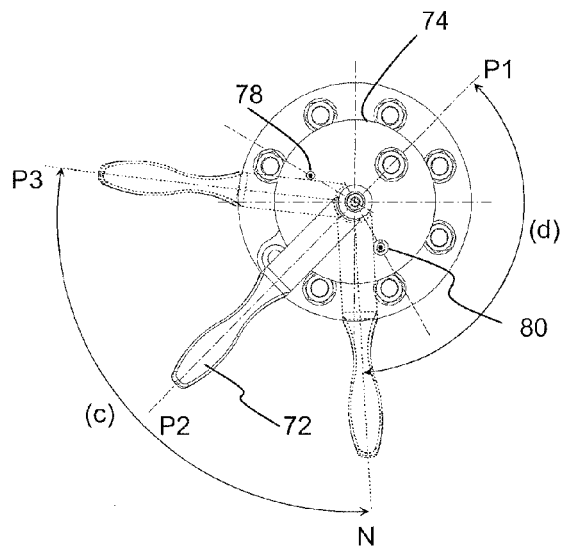
FIG. 4 is an end view in the direction of arrow B of the sampling device of FIG. 1.
Figure 5:
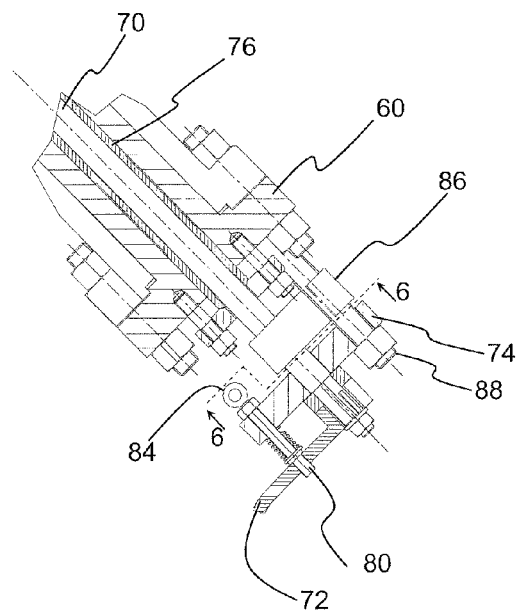
FIG. 5 is a larger-scale partial cross-sectional view of the lower end of the device of FIG. 1.

Preferably, it is desirable to have only one retractable stop 80 as shown in FIGS. 4 and 5. By way of example, this stop is made up of a rod 82 carried slidably by plate 74 and subjected to the action of an extension coil spring so that the end of this rod protrudes beyond the plate to stop the rotation of the lever.

In order to remove this stop and thus to allow passage of the lever, an action opposed to that of the force of the spring, such as a traction on end 84, allows retraction of the free end of the rod in the plate.

Figure 6:
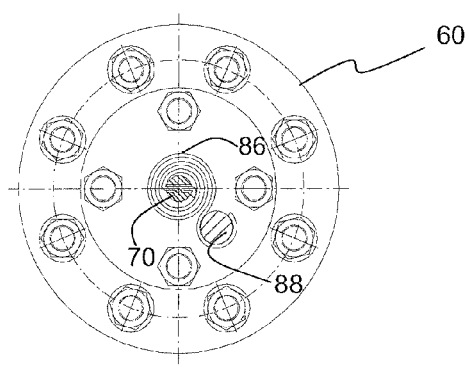
FIG. 6 is a radial cutaway view along line 6-6 of FIG. 5.

As shown in FIG. 6, a torsion spring 86 of spiral spring type allows rod 70 and cup 30 to return to a predetermined position. This spring is secured to the rod and to a pin 88 fastened to the body or the deflection member.

This predetermined position is advantageously the position identified by the neutral position (N) of the lever and of the cup.

Of course, without departing from the scope of the invention, the rotation of rod 68 and of cup 30 can be motorized.

The rod can therefore be connected to an electric or pneumatic geared motor, acting in both directions of rotation with an end position detection device for remaining within the cup clearance angular range (c). In this case, the presence of stops 78 and 80 is no longer required.

It is also possible to provide a cylinder fitted with a rack driving a pinion mounted on the rod. Since the piston stroke is limited by construction, return is provided by either a double-acting cylinder or a single-acting cylinder with an integrated spring.

Similarly, as illustrated in FIG. 1, it is possible to use a single-acting pneumatic cylinder 90 provided with an arch-shaped cam 92 secured to piston 94 whose stroke is limited by construction. Return of the cylinder is provided by a spring 96 integrated therein.

In position N of the lever, cam 92 is in radial contact with lever 72. When piston extension from cylinder 90 is required, the pressure in the suitable chamber of this cylinder generates a translational motion of extension of piston 94. As a result of this translational motion, the cam secured to piston 94 causes rotation of lever 72 as this piston is extending.

The difference between the diameter of the profile of cam 92 when it is at point N in contact with lever 72 and the diameter when piston 94 is fully extended allows rotation of the lever by a stroke (c) that does not cause sampling by device 14.

Once the piston extension command is stopped, the piston goes back to its initial position under the action of spring 96.

It can be noted that the sampling device can be operated manually at any time and at any operating stage of cylinder 90.

To form the sampling device, cup 30 is housed in housing 22. Bottom 26 is then added to this subassembly by matching bore 38 with perforation 42 in the bottom. The cover is then added with pin 34 matching blind bore 36.

As can be better seen in FIG. 2, recess 28 of cover 24 and recess 28' of bottom 26 are offset in relation to one another, diametrically offset here, so that there can be no communication through hollow 32 provided in cup 30.

Of course, the cover and the bottom are fastened to housing 22 by any known means, such as screwing or welding.

Once this subassembly formed, it is mounted and fastened to the upper end of tubular extension 44.

Then, the assembly made up of rod 68, the plate with stops 78 and 80, torsion spring 86 and lever 72 that controls the cup through the rod is fed into lower tubular extension 46.

During this introduction, the end of rod 68 is led to cooperate in rotation with bore 38 of cup 30 while being secured to this cup. Once this is completed, plate 74 is fastened to deflection member 50 as described above while taking care to tension the spiral spring by getting the end of this spring to lean on pin 88.

Under the effect of the spring, operating lever 72 rests against retractable stop 80 so that hollow 32 of the cup is in a position referred to as neutral, N (see FIGS. 2 and 4), i.e. with no communication between recesses 28 and 28', and by sealing recess 28 at the upper plane face thereof.

Once this assembly formed, body 18 carrying sampling head 16 is fed into enclosure 12 through pass-through hole 68 and it is fastened onto sole 66 by any known means, such as screw-bolt connection. Air lock 54 is then added and fastened to tubular pipe 52 of the body.

As better illustrated in particular in FIG. 2, hollow 32 of the cup can have several other positions in addition to the neutral position described above.

More precisely, hollow 32 can have a collection position (position P1) where this hollow 32 coincides with recess 28. In this position, a solid sample of same volume as the hollowed inner volume in the cup is transferred through gravity from the enclosure to hollow 32 of the cup, then sealed in the lower part thereof by the plane face of bottom 26.

The discharge position (position P2), here diametrically opposite the collection position, corresponds to the position where the hollow coincides with recess 28' of bottom 26 with transfer through gravity of the solid sample from the recess to the body of the sampling device, recess 28 being then sealed by the upper plane face of the cup.

Finally, a position of rest (position P3) where operating lever 72 rests against fixed stop 78 with a position of hollow 32 of the cup that allows no communication between recesses 28 and 28'.

Thus, during rotation of the lever and therefore of the cup, between position N and position P3, there is an angular range (c), referred to as no-load displacement, in which no solid sampling occurs.

During operation, from position N of the lever, the operator acts upon removable stop 80 on which the lever rests so that it retracts into the plate in order not to hinder the angular displacement of this lever. This operator actuates the lever and therefore the cup counter-clockwise with an angular displacement (d) between position N and position P1. When this position is reached, hollow 32 faces recess 28 of the cover and a solid sample present in the enclosure is collected in this hollow.

As soon as the recess contains a sufficient amount of solid, and while maintaining the stop in retracted position, the operator moves the lever (and the cup) with a 180° angular clearance, clockwise, so as to reach position P2 where hollow 32 coincides with recess 28' of the bottom. The solid contained in the hollow is then discharged through this recess and sent to body 18, then to the inlet of air lock 54 through tubular pipe 52, valves V1 to V3 being in closed position.

Advantageously, the removable stop is brought back to its initial position so as to prevent the cup from returning to collection position P1.

Valve V1 is then put in open position and the solid sample flows through tubular part 55 upstream from valve V3. The tubular part containing the sample is emptied and vented by opening, then closing valve V2. Finally, valve V3 is opened so as to recover the sample outside the enclosure in a suited vessel.

Of course, without departing from the scope of the invention, stop 78 can also be a removable stop similar to stop 80.

Thus, from position P1, the operator controls stop 78 so that it retracts in the plate and moves the lever with a 180° angular clearance, counterclockwise, so that it reaches position P2 with hollow 32 matching recess 28'.

After one sampling or a series of samplings, cup 30 is actuated under no-load conditions, without taking samples, through the agency of rod 70 and lever 72. This occurs through the displacement, in a single direction (clockwise or counterclockwise) or in both directions (clockwise and counterclockwise), of the lever and of the cup it controls between position N and position P3.

As better illustrated in part in FIG. 2, during this no-load travel, hollow 32 of the cup can be fully or partly in connection with recess 28' of bottom 26. On the other hand, it never coincides, even partly, with recess 28 of the cover. In this angular range (c), it is thus possible to actuate the cup with the desired frequency since no sample is taken in this range.

This no-load displacement thus allows preventing jamming of the moving parts, such as the cup, which may appear after long immobilization periods as a result of powder deposition, product agglomeration due to the nature of the chemical components, to the pressure and temperature conditions and to the exposure time in the enclosure.

Thus, for example, when the sampling device is used for taking samples of catalysts in a reforming unit whose catalyst regeneration is not continuous, catalyst sampling is carried out approximately every six months and it is recommended to perform at least one no-load displacement every week.

Of course, without departing from the scope of the invention, the sampling device can be applied for taking catalyst samples in an oil refining unit.

The invention claimed is:

1. A device for sampling a solid from a sealed enclosure, comprising a body carrying a sampling head with a solid collection recess, a collected solid transfer recess, an angularly rotatable shutter means for transferring the solid between the recesses and being controlled by a control means and means for limiting an angular rotation of the shutter means without loading of the shutter means.

2. A device for sampling as claimed in claim 1, wherein the control means comprises a rod connected to the shutter means and the means for limiting comprises stops and at least one of the stops being removable for limiting the angular displacement.

3. A device for sampling as claimed in claim 2, wherein the rod comprises a torsion spring which circumferentially bears the lever on one of the stops.

4. A device for sampling as claimed in claim 2, wherein the rod is connected to an operating lever cooperating with the stops.

5. A device for sampling as claimed in claim 4, wherein the rod comprises a torsion spring which circumferentially bears the lever on one of the stops.

6. A device for sampling as claimed in claim 1, wherein the control means comprises a rod connected to the shutter means and to a geared motor having two directions of rotation and being fitted with an end position detection device for limiting a no-load angular displacement of the shutter means.

7. A device form sampling as claimed in claim 1, wherein the control means comprises a rod connected to the shutter means and to a cam controlled by a cylinder.

8. A device for sampling as claimed in claim 1, wherein the control means comprises a rod connected to the shutter means and carrying a pinion cooperating with a rack carried by a cylinder and limitation of a no-load angular displacement of the shutter means is provided by a stroke of a piston of the cylinder.

9. A device for sampling as claimed in claim 1, wherein the shutter means comprises a cup provided with an axial hollow running through the cup.

10. A device for sampling as claimed in claim 1, comprising an enclosure to which the device is applied for taking samples isolated from an atmosphere outside the enclosure.

11. A device for sampling as claimed in claim 1, comprising an oil refinery unit to which the device is applied for taking catalyst samples.

12. A device for sampling as claimed in claim 1, comprising a reforming unit to which the device is applied for taking catalyst samples.

13. A device for sapling as claimed in claim 1, wherein the shutter means comprise a rotatable cup.

14. A method of use of a device for sampling a solid in a sealed enclosure comprising a sampling head with a solid collection recess, a collected solid transfer recess, an angularly rotatable shutter means for transferring the solid between the recesses and being controlled by a control means, comprising angularly rotating the shutter means to transfer the solid between the recesses without load by preventing jamming of the shutter means and/or of the control means.

15. A method of use of a device for sampling as claimed in claim 14, comprising performing the no-load angular displacement of the shutter means without collection of the solid through the sampling head.

16. A method of use of the device for sampling as claimed in claim 14, comprising periodically performing the no-load angular displacement.

17. A method of use of the device for sapling as claimed in claim 14, comprising weekly periodically performing the no-load angular displacement.

* * * * *